United States Patent
Izmailov (12)

(10) Patent No.: US 6,436,641 B1
(45) Date of Patent: Aug. 20, 2002

(54) METHOD AND APPARATUS FOR DNA SEQUENCING

(75) Inventor: Alexandre M. Izmailov, Etobicoke (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/550,467

(22) Filed: Apr. 17, 2000

(51) Int. Cl.$^7$ .................................................. C12O 1/68
(52) U.S. Cl. ........................ 435/6; 435/287.2; 204/456; 536/23.1; 702/20
(58) Field of Search .......................... 435/6, 91.1, 183, 435/287.2; 436/94, 800; 204/456; 536/23.1, 24.3; 702/19, 20

(56) References Cited

U.S. PATENT DOCUMENTS

| | | | | |
|---|---|---|---|---|
| 4,971,677 A | * | 11/1990 | Kambara et al. | 204/299 R |
| 5,062,942 A | * | 11/1991 | Kambara et al. | 204/299 R |
| 5,529,679 A | * | 6/1996 | Takahashi et al. | 204/603 |
| 5,674,743 A | * | 10/1997 | Ulmer | 435/287.2 |
| 6,004,446 A | * | 12/1999 | Middendorf et al. | 204/618 |
| 6,017,434 A | * | 1/2000 | Simpson et al. | 204/612 |

* cited by examiner

Primary Examiner—Bradley L. Sisson
(74) Attorney, Agent, or Firm—Oppedahl & Larson LLP

(57) ABSTRACT

The sequence of a target DNA molecule is determined by preparing four chain termination reaction mixtures, one for each base type. The first set of fragments, indicative of the positions of a first type of base, are labeled with a first fluorescent label. The second set of fragments, indicative of the positions of a second type of base, are labeled with a second fluorescent label different from the first fluorescent label. The third set of fragments, indicative of the positions of a third type of base, are labeled with a third fluorescent label, different from the first and second fluorescent labels or with at least two labels, including at least one fluorescent label selected from among the first, second and third fluorescent labels. The fourth set of fragments, indicative of the positions of a fourth type of base, are labeled differently from the third set of chain-termination fragments and with at least two different species of labels including at least one fluorescent label selected from among the first, second and third fluorescent labels. Thus, a total of only three fluorescent labels are required to label the DNA sequencing fragments. The first, second, third and fourth sets of chain-termination fragments are loaded onto the same lane of an electrophoresis separation medium and separated in an electric field. The separated fragments are detected in real-time as they migrate in the electrophoresis separation medium by irradiating the separated fragments with an excitation beam and collecting light emitted by the fluorescent labels in three optical channels. The signals from three optical channels are evaluated to determine a DNA sequence for the target species. This evaluation can be done with a specifically programmed computer.

7 Claims, 3 Drawing Sheets

METHOD AND APPARATUS FOR DNA SEQUENCING

FIELD OF THE INVENTION

This application relates to an improved method for determination of the sequence of DNA and to an apparatus for practicing such a method.

BACKGROUND OF THE INVENTION

Sequencing of nucleic acids using the chain termination method involves the general steps of combining the target nucleic acid polymer to be sequenced with a sequencing primer which hybridizes with the target nucleic acid polymer; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

Although this type of analysis was originally performed using radiolabeled fragments which were detected by autoradiography after separation, modem automated DNA sequencers generally are designed for use with sequencing fragments having a fluorescent label. The fluorescently labeled fragments are detected in real time as they migrate past a detector.

U.S. Pat. No. 5,171,534 which is incorporated herein by reference describes a variation of this basic sequencing procedure in which four different fluorescent labels are employed, one for each sequencing reaction. The fragments developed in the A, G, C and T sequencing reactions are then recombined and introduced together onto a separation matrix. A system of optical filters is used to individually detect the fluorophores as they pass the detector. This allows the throughput of a sequencing apparatus to be increased by a factor of four, since the four sequencing reaction which were previously run in four separate lanes or capillaries can now be run in one. However, it also requires the development of four compatible labels, and potentially complicated optical systems to allow discriminatory excitation and/or detection of these labels.

International Patent Publication No. WO97/40184 describes a method for increasing throughput of a DNA sequencer by altering the manner in which labels are applied to the various samples. In this method, each sample is first divided into four aliquots which are combined with four sequencing reaction mixtures. Each sequencing reaction mixture contains a polymerase enzyme, a primer for hybridizing with the target nucleic acid, nucleoside feedstocks and a different dideoxynucleotide. This results in the formation of an A-mixture, a G-mixture, a T-mixture and a C-mixture for each sample containing product oligonucleotide fragments of varying lengths. The product oligonucleotide fragments are labeled with fluorescent tags, and these tags will generally be the same for all four sequencing reactions for a sample. However, the fluorescent tags used for each sample are distinguishable one from the other on the basis of their excitation or emission spectra. Next, the A-mixtures for each sample are combined to form a combined A mixture, the G-mixtures are combined to form a combined G-mixture and so on for all four mixtures. The combined mixtures are loaded onto a separation matrix at separate loading sites and an electric field is applied to cause the product oligonucleotide fragments to migrate within the separation matrix. The separated product oligonucleotide fragments having the different fluorescent tags are detected as they migrate within the separation matrix.

Nelson et al., "DNA Sequencing of four bases in three lanes" *Nucleic Acids Res.* 20: 1345–1348 (1992) and Nelson et al., "Sequencing two DNA Templates in five channels by digital compression" *Proc. Natl Acad. Sci. (USA)* 90:1647–1651 (1993) discuss the use of numerical coding approaches to reduce the number of lanes of a gel necessary to determine a DNA sequence. Reductions to 3 lanes or 2.5 lanes are achieved, respectively, by mixing combinations of dideoxy terminators in the various reactions.

SUMMARY OF THE INVENTION

The present invention provides an alternative approach to improving the throughput of a sequencing apparatus. Furthermore, the present invention makes it possible to explicitly determine the positions of all four bases in a single lane of a separation medium while utilizing only three fluorescent labels. In accordance with the invention, the sequence of a target DNA molecule is determined by preparing four chain termination reaction mixtures, one for each base type, as follows:

(a) a first set of chain-termination fragments indicative of the positions of a first type of base, wherein the fragments in the first set of fragments are labeled with a first fluorescent label;

(b) a second set of chain-termination fragments indicative of the positions of a second type of base, different from the first type of base, wherein the fragments in the second set of fragments are labeled with a second fluorescent label different from the first fluorescent label;

(c) a third set of chain-termination fragments indicative of the positions of a third type of base, different from the first and second types of bases, wherein the fragments in the third set of fragments are labeled with a third fluorescent label, different from the first and second fluorescent labels or with at least two labels, including at least one fluorescent label selected from among the first, second and third fluorescent labels; and (d) a fourth set of chain-termination fragments indicative of the positions of a fourth type of base, different from the first, second and third types of bases, wherein the fragments in the fourth set of fragments are labeled differently from the third set of chain-termination fragments and with at least two different species of labels including at least one fluorescent label selected from among the first, second and third fluorescent labels. Thus, a total of only three fluorescent labels are required to label the DNA sequencing fragments.

The first, second, third and fourth sets of chain-termination fragments are loaded onto the same lane of an electrophoresis separation medium and separated in an electric field. The separated fragments are detected in real-time as they migrate in the electrophoresis separation medium by irradiating the separated fragments with an excitation beam and collecting light emitted by the fluorescent labels in three optical channels. The signals from three optical channels are evaluated to determine a DNA sequence for the target species.

A further aspect of the present invention is an apparatus adapted for performing sequencing in accordance with this methodology. Such an apparatus has a separation medium holder, and a power source and electrodes for applying an electric field to separation medium. The apparatus also has one or more excitation sources and optical systems appropriate for directing the excitation light to detection sites in the separation medium; and detectors for detecting light in three optical channels, one for detection of each of the three labels. The time-domain signals from the three optical channels are analyzed using a computer processing system, which can be located in the same housing as the balance of the electrophoresis apparatus or in a separate apparatus which receives the signal from the electrophoresis apparatus.

DETAILED DESCRIPTION OF THE INVENTION

Figure 1:
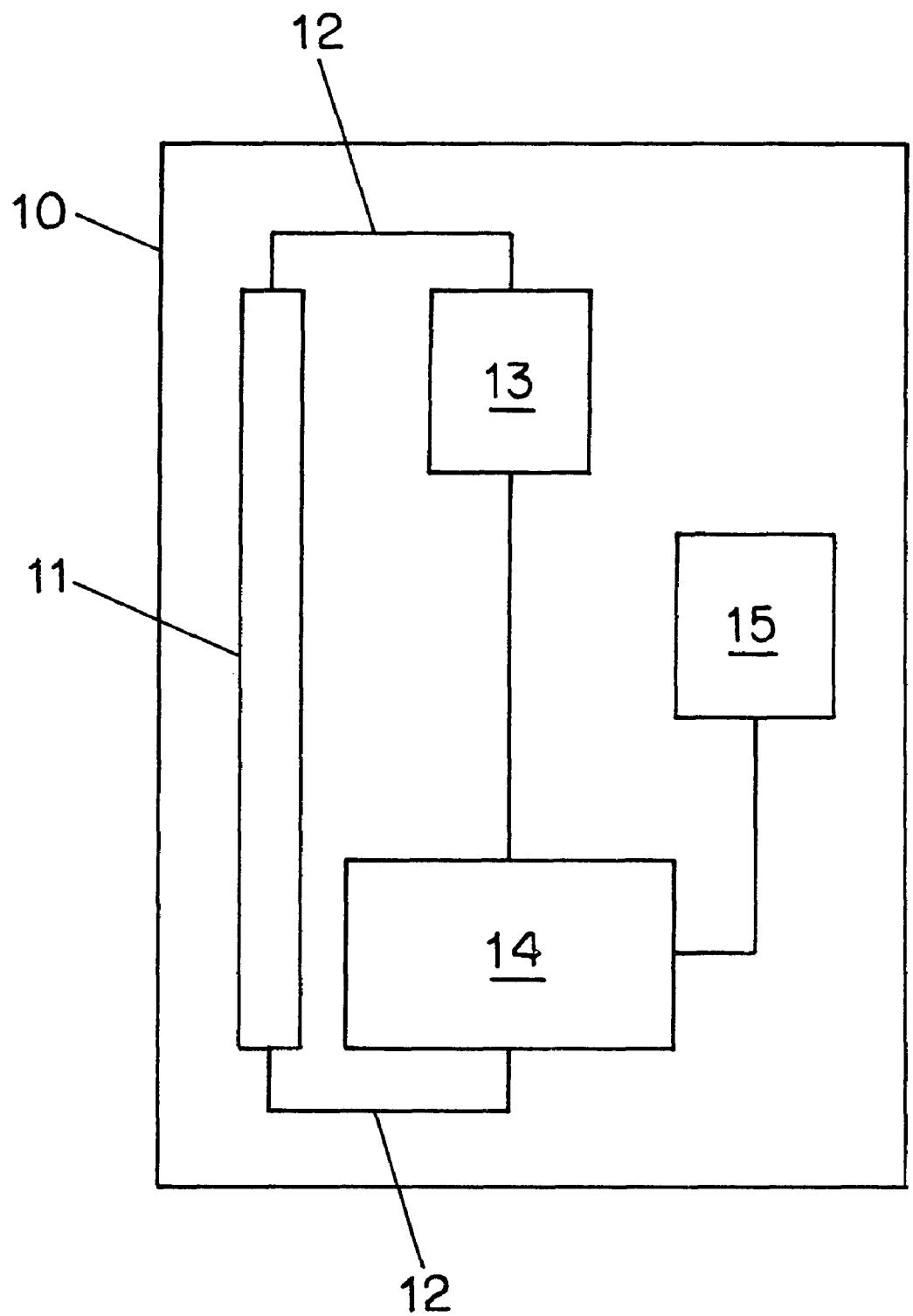
FIG. 1 shows a schematic representation of an apparatus in accordance with the invention.

The present invention provides a method and apparatus for the sequencing of a target nucleic acid polymer. The invention is designed to work with the fragment sets created in chain termination sequencing method, although it would work equally well with any other methodology which generates similar fragment sets. As is well known in the art, in chain termination sequencing, a template-dependent polymerase reaction is used to extend a primer. The extended primer is terminated by incorporation of chain terminating nucleotide triphosphate analogs such as dideoxynucleotide triphosphates, which results in the generation of a set of sequencing fragments for each base type indicative of the positions of that base. Thus, as used in the specification and claims hereof, the phrase "set of chain-ternination fragments" refers to a mixture of polynucleotide fragments of varying lengths, wherein the lengths of the fragments within a set are indicative of the positions of a selected type of base in a target polynucleotide being sequenced.

The fragments within each set of chain-termination fragments are labeled with a fluorescent label. As used herein, the term "fluorescent labels" refers generally to molecules which emit light at an emission wavelength following excitation of the label with light of an excitation wavelength. The label may also be a molecule which emits light as a result of a chemiluminescent or enzyme reaction. Examples of specific materials which can be used as fluorescent labels include organic dyes such as cyanine dyes, rhodamine dyes, fluorescein and fluorescein derivatives, and chelates of ions of rare-earth metals. Appropriate fluorescent label(s) as discussed below are incorporated into the polynucleotide fragments of each set of chain-termination fragments. The fluorescent label can be incorporated by attaching it to the primer which is extended, or through the use of fluorescently-labeled chain terminating nucleotide triphosphate analogs. The fluorescent label could also be incorporated with the extending polymer by attaching it to non-terminating nucleoside triphosphates. Labels which can be incorporated in this way are known, for example from WO93/03 180, although this approach requires greater care in the experimental set up to maintain the intensity of each label type at comparable levels.

The key element of the present invention is the manner in which three fluorescent labels are used to label the four sets of chain-termination fragments to permit sequence determination when the mixture is resolved in a single lane of a separation medium, such as an electrophoresis gel. This is achieved through the use of double-labeling of at least one and in some cases two of the reaction mixtures. "Double-labeling" within the scope of the invention can be achieved in various ways. First, a set of fragments can be double-labeled through the incorporation of a label on the primer and a label on the terminator. Alternatively, a second label for use in combination with either a labeled primer or a labeled terminator can be incorporated through the use of labeled non-terminating nucleosides. Double-labels can also be attached to any of the individual labelable components of the reaction (i.e, primers, terminators or non-terminating nucleosides). As discussed in more detail below, the benefits of double-labeling can also be accomplished through a "virtual" double-labeling, in which a mixture of fragments containing two labels is prepared. This would be accomplished, for example, using two species of differently labeled, but otherwise identical primers, or two species of differently labeled but otherwise identical terminators, or two species of differently labeled but otherwise identical non-terminating nucleosides in the preparation of a fragment set. The advantages of virtual double-labeling are simplification of chemistry, better stability of labeled fragments, and more equal electrophoretic mobilities between single and double-labeled species. The relative intensity of the labels can be easily manipulated by changing the relative amounts of the two labels. In addition, one does not have to be concerned with interactions between labels.

For purposes of the discussion which follows, the invention will be exemplified with references to three cyanine dyes, which are sold under the tradenames CY5, CY5.5 and CY7. The use of these dyes offer various advantages which will be discussed below. It should be understood, however, that other combinations of fluorescent labels could be used, and that the advantages described are not unique to this trio of cyanine dyes.

A fundamental advantage of the method of the invention is the fact that it requires only three dyes. When selecting dyes for use in a four-dye sequencing system (i.e, all four base types are labeled differently and run in one lane), one of the findamental challenges is identifying a set of four dyes which have comparable effects on the electrophoretic mobility of the polynucleotides to which they are attached and which have excitation and/or emission spectra which are sufficiently different to allow discrimination between them. Where the emission spectra are distinguishable (a preferred circumstance), one faces the further challenge of identifying four dyes with comparable excitation spectra, such that the same light source can be used for all excitations with reasonably equal efficiency. Use of multiple excitation sources (especially in multilane sequencer with individual excitation sources for each lane) makes the optical assembly extremely complicated. These challenges are greatly reduced when only three dyes are used.

Table 1 shows an exemplary labeling scheme in accordance with the invention.

TABLE 1

| Base | Primer Label | Dye Terminator |
| --- | --- | --- |
| A | CY5 | — |
| C | CY5.5 | — |
| G | CY5 | CY7 |
| T | CY5.5 | CY7 |

The samples labeled as above are loaded in the same lane of an electrophoresis separation medium. High voltage is applied, which causes the fragments to migrate and separate.

The migration rate is based predominantly on the size of the fragments, such that smaller fragments arrive earlier at a detection site. When the fragments reach the detection site, they are illuminated by light of one or more wavelengths (depending on the characteristics of the labels selected), and the light emitted is captured in an optical system having three optical channels, one for each of the three labels. As summarized in Table 2, the peaks which are detected in each of the three optical channels provide an indication of which base a given peak is associated with.

TABLE 2

| Base | CY5 Channel | CY5.5 Channel | CY7 Channel |
|---|---|---|---|
| A | + | — | — |
| C | — | + | — |
| G | + | — | + |
| T | — | + | + |

Thus, a peak detected by the CY5 channel indicates that the base is either an A or a G. The CY7 channel allows these two choices to be distinguished, since in this particular configuration there would also be a peak in the CY7 channel for a G, but not for an A.

Tables 3 and 4 show alternative labeling scheme within the scope of the invention.

TABLE 3

| Base | Primer Label | Dye Terminator |
|---|---|---|
| A | CY5 | — |
| C | CY5.5 | — |
| G | CY7 | — |
| T | CY5 or CY5.5 | CY7 |

TABLE 4

| Base | Primer Label | Dye Terminator |
|---|---|---|
| A | CY5 | — |
| C | CY5.5 | — |
| G | CY7 | — |
| T | CY5 or CY5.5 | CY5.5 or CY5 |

The difference between the labeling scheme in Table 1 and those in Tables 3 and 4 is that in the latter two tables the fragments for only one type of base are double-labeled. This may simplify the cost of sample preparation and thus the cost of analysis.

It should be appreciated in connection with Tables 1–4 that there is no special relationship between the base and the label. Thus, while the A fragment mixture is shown as being labeled with CY5 in each of the tables, there is nothing special about the combination and the A fragments might just as well be labeled with CY5.5 or CY7. In fact, in order to reduce the possibility of mistakes during heterozygote analysis, it is desirable to perform forward and reverse runs with a different nucleotide or pair of nucleotides having double labeling. For example if the T's and G's are double-labeled in the forward direction, and A's and C's are double-labeled in the reverse direction.

It will also be appreciated that while the tables show the predominant use of primer labels, this is not required, and the predominant labeling technique could be dye terminators or some other labeling technique. A combination of labeling techniques could also be used. Thus, as shown in Table 5, some of the single-labeled fragment sets could be labeled with one technique while others are labeled by another.

TABLE 5

| Base | Primer Label | Dye Terminator |
|---|---|---|
| A | CY5 | — |
| C | — | CY5.5 |
| G | CY7 | — |
| T | CY5 or CY5.5 | CY5.5 or CY5 |

In a further embodiment of the invention, the double-labeled sets of fragments are double labeled through the use of double-labeled primers. Attachment of two fluorescent labels to the primer can be done by including a modified base during primer synthesis. Such a technique is described in Wang et al., *Electrophoresis* 17: 1485–1490 (1996). In this case, it is desirable to avoid creation of energy transfer systems, where the energy absorbed by one label is transferred to the other, since the goal is to have simultaneous emission from both. This should not be a difficulty, however, since the creation, not the avoidance , of energy transfer systems is normally the challenge.

Finally, it is possible to achieve double labeling through the simultaneous use of two different species of primers or terminators which differ from one another in the label employed. Thus, for example, if one is double-labeling for the base T, part of the primers employed might by labeled with CY5 and the other part with CY5.5. While the portions could be a 50:50 mixture of the two labels, since one of the two labels functions predominantly as a reference, the actual mixture might be 80:20, 90:10 or some other combination appropriate for providing a "signal" label and a "reference" label.

The sequencing method of the invention is suitably performed in an apparatus specifically adapted for the collection and interpretation of sequencing data traces. As shown in FIG. 1, such an apparatus comprises a housing 10 which receives an electrophoresis separation medium, for example a polyacrylamide gel 11 in juxtaposition with electrodes 12 for applying an electric field to the separation medium. The electrodes 11 are in turn connected to a power supply 13. These components, and other components conventionally employed in such devices (for example heating plates) are collectively referred to as an "electrophoresis apparatus." Also within the housing 10 is an optical section 14. The optical section 14 includes detectors associated with each of the three optical channels. These detectors provide a signal which is interpreted by a programmed data processor 15 using an appropriate logic table of the type shown in Table 2. The data processor 15 may be disposed within the housing 10 as shown, or it may be located in a separate piece of apparatus. In the latter case, communication between the optical section 14 and the separate piece of apparatus may be via a wired connection or a non-wired (for example a radio link or physical transfer of a diskette).

Figure 2:
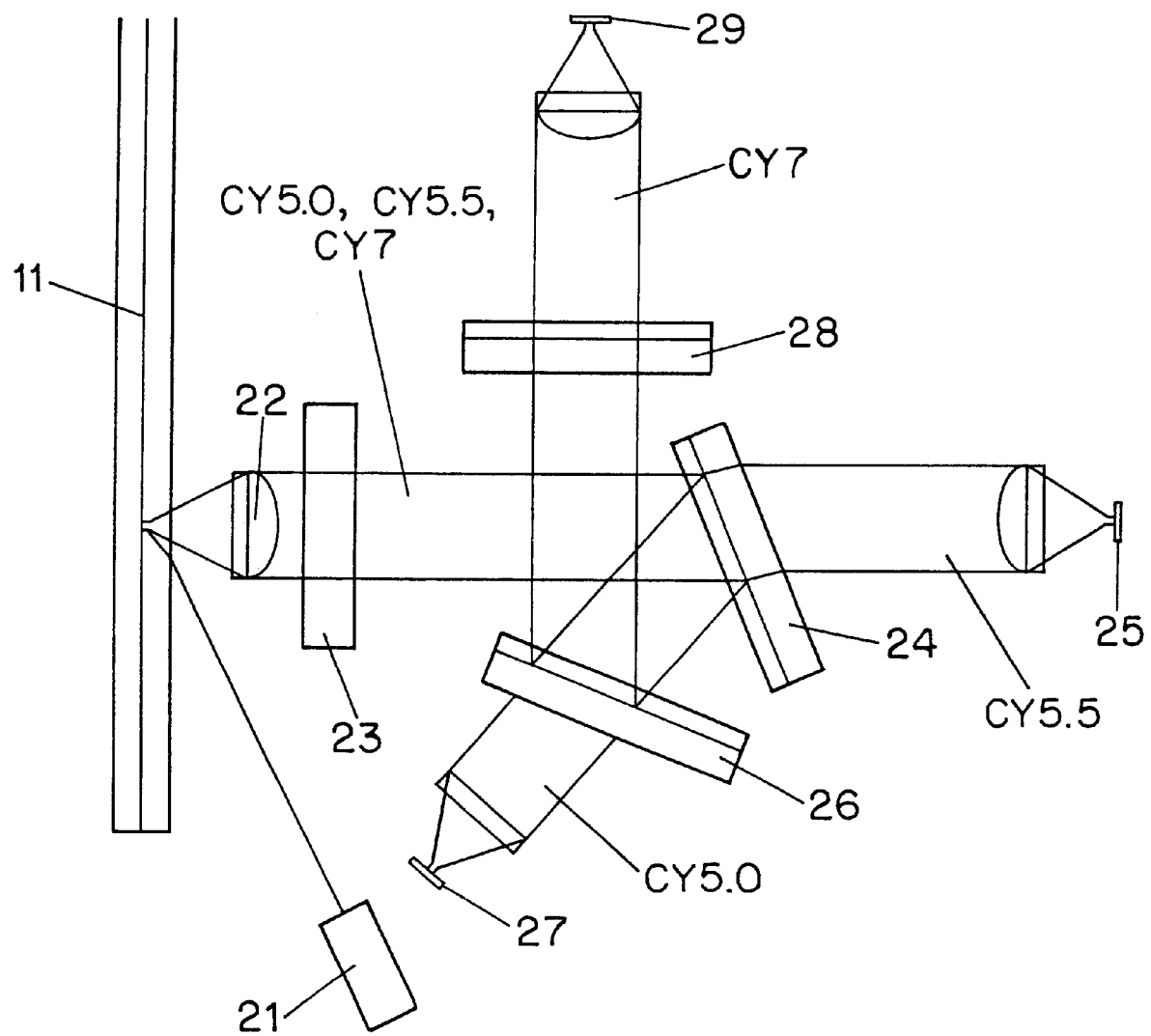
FIG. 2 shows the optical section of an embodiment of an apparatus in accordance with the invention.

An exemplary embodiment of the optical section 14 is shown in more detail in FIG. 2. A laser excitation source 21 is position to irradiate a detection site on gel 11. In the case of CY5, CY5.5 and CY7, a single 635 nm laser diode excitation source (for example, Sanyo DL3148-011 or DL3148-033 ) can be employed. Emitted light is collected through lens 22 and passed through filter 23 to reduce scattered light of the excitation wavelength. A suitable filter in the specific embodiment when the labels are CY5, CY5.5 and CY7 and the excitation source is a 635 nm laser diode is an RG645 glass filter (Omega Optical, Inc., Brattleboro, Vt). The light which passes through filter 23 impinges on a first interference filter 24 which transmits light of a wavelength corresponding to one of the labels and reflects other wavelengths. A first detector such as photodiode 25 is positioned to detect the light transmitted by the first filter 24. When the first filter is a 715DF30(T) interference filter (Omega Optical, Inc.), the first filter 24 and the first detector together make up the CY5.5 optical channel. The light which is reflected by the first filter 24 is directed to a second filter 26 which transmits light of a wavelength corresponding to another of the labels and reflects other wavelengths. A second detector such as photodiode 27 is positioned to detect the light transmitted by the second filter 26. When the second filter is a 875DF1 8(T) interference filter (Omega Optical, Inc.), the second filter 26 and the second detector together make up the CY5 optical channel. The light which is reflected by the second filter 26 is directed to a third filter 28 which transmits light of a wavelength corresponding to the remaining label. A third detector such as photodiode 29 is positioned to detect the light transmitted by the third filter 28. When the third filter is a 770DF40 interference filter (Omega Optical, Inc.), the third filter 28 and the third detector together make up the CY7 optical channel.

Figure 3:
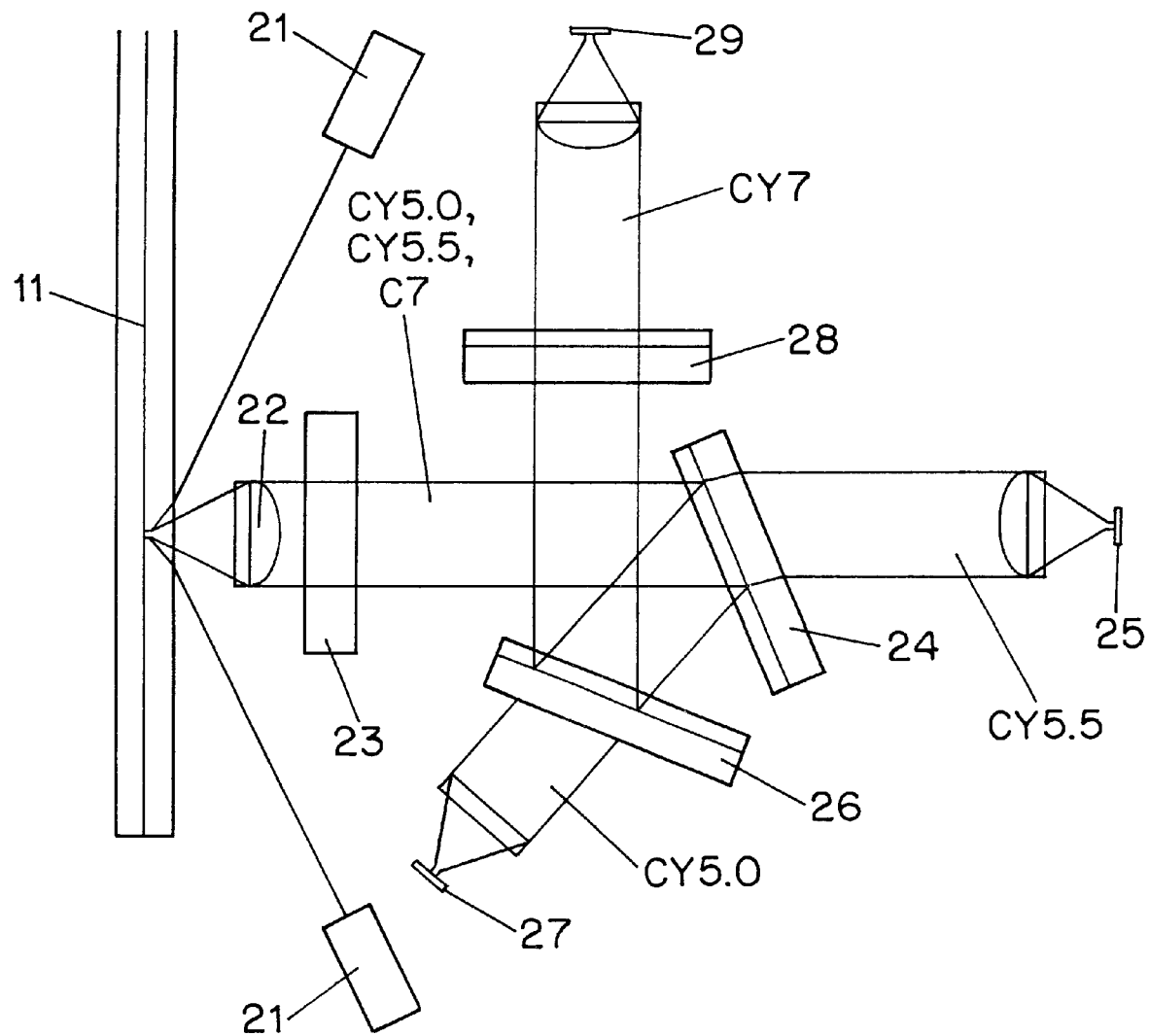
FIG. 3 shows the optical section of another embodiment of an apparatus in accordance with the invention.

When an apparatus with a single excitation source (or a single excitation source per lane) is employed with CY5, CY5.5 and CY7 as the labels, the sensitivity of the CY7 channel will be lower because of the lower excitation efficiency of CY7 at the wavelength of the laser diode. As a result, the peaks associated with CY7 will be smaller. This need not be a significant drawback, however, because in the labeling scheme set forth in Table 1 CY7 is used as a "reference" label and need not be actually evaluated as a "signal" label for base-calling. Of course, one alternative to this loss of sensitivity is to compensate for it by increasing the badwidth of the filter used for the third channel. Another way is to employ more than one excitation source so that each of the labels employed will have good excitation and emission efficiency. FIG. 3 shows a variation of the optical section of FIG. 2 in which two laser sources are included. For CY7, a suitable second laser would be a laser diode with a wavelength of 750 nm.

The data processor of the invention may be a dedicated microprocessor, or a general purpose computer (such as a PC or a mini-computer) running a set of program instructions. In either case, the data processor takes the three data streams from the three channels of the optical system and evaluates them in accordance with a logic table appropriate to the labeling scheme employed. The data processor may also perform appropriate peak selection and normalization routines in order to improve the accuracy of the final base-calling result. Such processes are described in commonly assigned U.S. Pat. Nos. 5,853,979, 5,916,747 and 5,981,186, which are incorporated herein by reference. In addition, when a real as opposed to a virtual double-labeling system is used, it must be remember that the increase in size of the double-labeled fragments will result in a decrease in the electrophoretic mobility. This leads to misalignment of the traces for samples loaded in the same lane. However, the delay in the appearance of double-labeled bands can be compensated for by means of calculation, or by attaching an additional label to the single-labeled moieties. This additional label need not be fluorescent or have any other particular properties, because it is used solely to compensate for the differences in mobility. The additional label should, however, have approximately the same molecular weight as te dye molecule which is used as the secondary label.

The foregoing discussion of the apparatus describes the component parts in terms of excitation sources and filters which are compatible with the labels CY5, CY5.5 and CY7. It will be appreciated, however, that the excitation source can be selected from any suitably intense light source, including lasers (such as 632.8 nm He—Ne laser) and other laser diodes, which provides light at a wavelength effective to serve as an excitation wavelength for the labels employed. The excitation sources are suitably employed as laser diode modules, which include a laser diode and a focusing lens. The lens concentrates light emitted by the laser diode. Modules of this type are commercially available, for example for Electron Co., Ltd., Taiwan.

What is claimed is:

1. An apparatus for obtaining information for use in sequencing of DNA comprising:

(a) an electrophoresis apparatus comprising a separation medium for separation of sets of chain termination fragments in at least one lane; and (b) an optical section comprising
   at least one excitation source disposed in relation to the electrophoresis apparatus to provide excitation energy to fragments at a detection site in the lane in the separation medium;
   a detector system disposed in relation to the electrophoresis apparatus to detect emitted light from the detection site, said detector system having exactly three optical channels for production of three data signals in response to emitted light of three different wavelengths emitted from the detection site in the lane.

2. An apparatus for sequencing DNA comprising:

(a) an electrophoresis apparatus comprising medium for separation of sets of chain termination fragments in at least one lane;

(b) an optical selection comprising
   at least one excitation source disposed in relation to the electrophoresis apparatus to provide excitation energy to fragments at a detection site in the lane of the separation medium;
   a detector system disposed in relation to the electrophoresis apparatus to detect emitted light from the detection site, said detector system having three optical channels for production of three data signals in response to emitted light of three different wavelengths emitted from the detection site in the lane; and (c) a data processor operatively connected to receive the three data signals from the three optical channels, and to process the three data signals into a complete DNA sequence in which the positions of all four bases are explicitly determined.

3. The apparatus of claim 2, wherein the detector system has exactly three optical channels.

4. The apparatus of claim 3, wherein the data processor evaluates each peak location in the three data signals and for any given peak location assigns a peak as a first base type when there is a peak only in the first data signal, as a second base type when there is a peak only in the second data signal, as a third base type when there are peaks in the first data signal and the third data signal, and as a fourth base type when there are peaks in the second data signal and the third data signal.

5. The apparatus of claim 3, wherein the data processor evaluates each peak location in the three data signals and for any given peak location assigns a peak as a first base type when there is a peak only in the first data signal, as a second base type when there is a peak only in the second data signal, as a third base type when there is a peak only in the third data signal, and as a fourth base type when there are peaks in two of the first, second or third data signals.

6. The apparatus of claim 2, wherein the data processor evaluates each peak location in the three data signals and for any given peak location assigns a peak as a first base type when there is a peak only in the first data signal, as a second base type when there is a peak only in the second data signal, as a third base type when there are peaks in the first data signal and the third data signal, and as a fourth base type when there are peaks in the second data signal and the third data signal.

7. The apparatus of claim 2, wherein the data processor evaluates each peak location in the three data signals and for any given peak location assigns a peak as a first base type when there is a peak only in the first data signal, as a second base type when there is a peak only in the second data signal, as a third base type when there is a peak only in the third data signal, and as a fourth base type when there are peaks in two of the first, second or third data signals.

* * * * *